United States Patent [19]

Szekely et al.

[11] 4,176,122
[45] Nov. 27, 1979

[54] PROCESS FOR THE PREPARATION OF BICYCLIC ENONE COMPOUNDS

[75] Inventors: István Székely, Szentendre; István Tömösközi, Budapest; Gábor Kovács, Budapest, Vilmos Simonidesz, Budapest; Marianna Lovász née Gáspar, Budapest; Borbála née Ördög Keresztes, Budapest; Julia née Rádóczi Remport, Budapest; István Stadler, Budapest; Zsuzsa née Gombos Visky, Budapest; Csaba Szántay, Budapest, all of Hungary

[73] Assignee: Chinoin Gyogyszer es Vegyeszeti Termekek, Budapest, Hungary

[21] Appl. No.: 770,997

[22] Filed: Feb. 22, 1977

[30] Foreign Application Priority Data

Feb. 23, 1976 [HU] Hungary .............................. CI 1645

[51] Int. Cl.$^2$ ............................................ C07D 307/93
[52] U.S. Cl. ......................... 260/343.3 P; 260/346.22
[58] Field of Search .................. 260/343.3 P, 346.2 R, 260/598, 603 C, 346.22

[56] References Cited

U.S. PATENT DOCUMENTS

| 3,864,387 | 2/1975 | Nelson | 260/343 P |
| 3,901,896 | 8/1975 | Albright | 260/598 |

OTHER PUBLICATIONS

Corey et al., J. Org. Chem., vol. 38, p. 1233, 1973.
Corey et al., Tetrahedron Letters No. 31, pp. 2647–2650.

*Primary Examiner*—John M. Ford
*Assistant Examiner*—Jane T. Fan
*Attorney, Agent, or Firm*—Karl F. Ross

[57] ABSTRACT

A process for the preparation of bicyclic enon compounds in which a lactone diol is selectively oxidized to obtain a hydroxy-aldehyde with one hydroxyl group and, without isolation, the hydroxy-aldehyde is reacted with a phosphorus compound. The reaction product can be acylated or silylated.

8 Claims, No Drawings

PROCESS FOR THE PREPARATION OF BICYCLIC ENONE COMPOUNDS

The present invention provides an economic and simple process for the preparation of compounds of the formula V

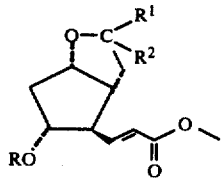

(V)

wherein
R is hydrogen conventional, acyl, or silyl,
$R^1$ and $R^2$ together form an oxo group, or
$R^1$ is lower alkoxy which can be substituted with one, two or three halogen atom(s), and
$R^2$ is hydrogen,
Q is straight or branched-chain alkyl having one to 10 carbon atoms, alkenyl having one double bond or alkinyl having one triple bond.

According to the invention the above compounds are prepared by reacting a racemic or optically active lactone diol derivative of the formula III

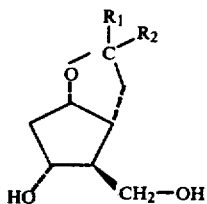

(III)

with an oxidant, and then reacting the thus obtained aldehyde of the formula II

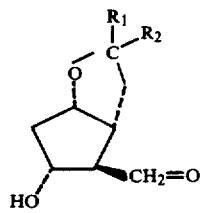

(II)

preferably without isolation, with a phosphorous compound of the formula VI

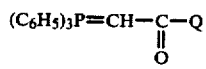

(VI)

or VII

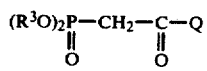

(VII)

wherein $R^3$ is lower alkyl.

The hydroxyl group of formula VIII can then be subjected to alkylating, acylating or silylating.

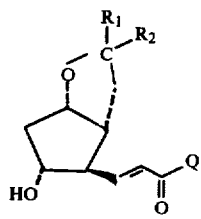

(VIII)

Optically active compounds of the formula V can be formed by resolution of a racemic compound of the formula V.

The significance of our process is that it provides a simple synthesis which can be stereochemically controlled, with outstanding economic results. This advantage is partly due to the fact that the starting materials of the two-step direct synthesis of the prostaglandine intermediate of the formula I

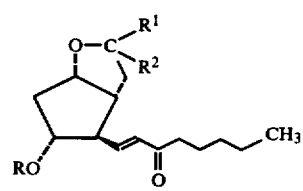

(I)

are readily available.

The crucial reaction step of the process according to the invention is the selective oxidation wherein care must be taken not to involve the other hydroxyl group when the prime hydroxyl is oxidized. There are a number of methods known in the art for the transformation of the hydroxymethyl group into an aldehyde group [See for example: Collins reagent: Tetrahedron Lett., 3363 (1968), J. Org. Chem. 35, 4000 (1970); chromium complexes: Chemistry and Industry, 1594 (1969), Tetrahedron Lett., 2647 (1975); oxidation of sulfide or sulfoxide type: J.A.C.S. 94, 7586 (1972), Tetrahedron Lett., 919 (1973), J. Org. Chem. 38, 1233 (1973) and J.A.C.S. 87, 5661 (1965)]. According to our experiments the thioanisole-chloro complex proved to be the most advantageous although we could use also other oxidants, for example the Collins reagent or a chromium complex but with a worse selectivity. The other factor which limitates the conditions of the oxidation is the inherent lability of the hydroxy aldehyde of the formula II that is prepared.

The existence of the desired intermediate of the formula II is a spectroscopically verified fact. We succeeded also in isolating the compounds of the formula II on a chromatographic column but the compounds themselves proved to be very labile although their isolation in form of their stabile derivatives (for example a hydrosulfide adduct) was possible.

The observations we made were in agreement with the results of E. J. Corey et al. who characterized the β-hydroxy-aldehyde derivatives of the formula II as very labile compounds, which are not separable by chromatography carried out at room temperature (Tetrahedron Lett., 307 (1970)). Surprisingly, we found that the stabile compounds of the formula I, wherein R is hydrogen, are obtained with an excellent yield when the intermediates of the formula II, obtained by oxidation, are reacted immediately, without separation, with the phosphorous compound necessary to the olefin synthesis, thus with triphenyl-n-hexanoyl-methylenephosphorane or with the anion derived from dimethoxy-2-oxoheptylphosphonate.

By acylating the raw product or the reaction mixture, crystalline products of the formula I (for example where R is a para-phenyl-benzoyl group) may be isolated.

The decomposition of the compounds of the formula II has not been observed under the above conditions, a result most probably due to the formation of an adduct between the compounds of the formula III and the thioanisole-chloro complexes in the first step of the oxidation. The oxidation proceeds only when a base for example triethyl amine is added to the reaction mixture.

In other words the unstable hydroxy-aldehydes of formula II are "captured" immediately after their formation using oxo-reagents of the phosphorane or phosphonate type and thus these unstabile molecules exist only for a very short time.

In one of our earlier patent applications (Hungarian patent application No. CI 1448) we have already described the use of oxo-reagents of phosphorane type for carrying out a direct reaction in mixtures obtained by oxidizing lactone alcohols of the formula III, protected in the 5α-position with an RO-group, wherein R is acyl, alkyl or silyl, $R^1$ and $R^2$ are an oxo group. In the present application hydroxy aldehydes of the formula II, having different chemical character, are reacted in the nascent state with an oxo reactant of the phosphorane or phosphonate type.

To sum up what has been said, in the process according to the present invention preferably the readily available lactone or protected lactol diols of the formula III are used as starting materials. The starting compounds are reacted with a thioanisole-chloro complex reactant at about −20° C., using dichloromethane-acetonitrile or dichloro methane-carbon tetrachloride-dimethyl sulphoxide as aprotic solvent mixtures. Triethyl amine is added to the mixture, preferably at about −30° C. and triphenyl-n-alkanoylmethylene-phosphorane or the anion formed from dimethoxy-2-oxo-alkyl-phosphonate is immediately added. The mixture is allowed to stand overnight, whereupon the obtained compound of the formula I, wherein R is a hydrogen, $R^1$ and $R^2$ stand for an oxo group or $R^1$ represents an alkoxy group and $R^2$ stands for a hydrogen, is isolated by chromatography or the side products are precipitated with petroleum ether after acylating the reaction mixture and the product remained in the solution is recrystallized from isopropanol upon evaporation.

The physical-chemical characteristics of the intermediates of the general formula I prepared according to the present invention are identical with those of the compounds prepared by other procedures. Further details of our process are to be found in the following Examples which are, however, for illustration only.

EXAMPLE 1

3,3aβ,4,5,6,6aβ-hexahydro-2-oxo-4β-(3-oxo-trans-1-octene-1-yl)-5α-hydroxy-2H-cylopenta[b]furane 0.825 g. (0.0116 moles) of chlorine in 12 ml. of carbon tetra chloride are cooled down to −30° C. and the solution of 1.44 g. (0.0116 moles) of thioanisole in 10 ml. of dry dichloromethane is added. The obtained suspension (thioanisole-chloro complex) is allowed to stir at −10° C. for 10 minutes, and then 1 g. (0.0058 moles) of 3,3aβ,4,5,6,6aβ-hexahydro-2-oxo-4β-hydroxymethyl-5α-hydroxy-2H-cyclopenta[b]furane dissolved in the mixture of 20 ml of dry dimethyl sulfoxide and 20 ml. of dry dichloromethane, is added dropwise, at −30° C. The suspension dissolves slowly. The reaction mixture is allowed to stir at −20° to −21° C. for five hours. By adding triethyl amine to an aliquot sample of the reaction mixture and carrying out t.l.c. measurement (3:1 mixture of ethyl acetate-methanol) the reaction can be controlled.

2.3 g. (0.0232 moles) of triethyl amine in 10 ml of dichloromethyne are added dropwise to the reaction mixture at −20° C., and then immediately 3.25 g. (0.0087 moles) of triphenyl-n-hexanoylmethylene-phosphorane in 10 ml. of methylene chloride are added. The reaction mixture is allowed to warm to room temperature, allowed to stir at this temperature for 3 hours, then to stand overnight. The reaction mixture is washed with brine, the organic phase is dried over sodium sulfate and evaporated under reduced pressure. 6 g. of a thick oil are obtained, which is passed through 60 g. of silica gel using a 2:1 mixture of ethyl acetate and petroleum ether as eluent. The fractions corresponding to $R_f$=0.47 are collected and evaporated under reduced pressure. The named compound is obtained in the form of a pale yellow oil. Yield: 0.9 g. (58.3%), $R_f$=0.47 (ethyl acetate-petroleum ether 2:1). IR spectrum (film: 3400 (—OH), 1770 (=CO lactone), 1670, 1700 (s-cis s-trans enon), 1630 (>C=C<), 975 (trans —CH=CH—) cm$^{-1}$ NMR spectrum (CDCl$_3$)=6.8−6.05 (d+dd, 2 H, olefin)

4.98 (m, 1H, —CHO—), 4.15 (m, 1H, —ĊHOH).

EXAMPLE 2

3,3aβ,4,5,6,6aβ-hexahydro-2-oxo-4β-(3-oxo-trans-1-octene-1-yl)-5α-hydroxy-2 H-cyclopenta[b]furane The process described in Example 1 is used with the only difference that the corresponding compound of formula III is dissolved in 15 ml. of acetonitrile instead of dimethyl sulfoxide. Yield: 1.05 g.(67.7%).

The physical-chemical characteristics of the obtained product are identical with those of the named compound of the Example 1.

EXAMPLE 3

3,3aβ,4,5,6,6aβ-hexahydro-2-oxo-4β-(3-oxo-trans-1-octene-1-yl)-5α-hydroxy-2 H-cyclopenta[b]furane (procedure of phosphonate type)

0.825 g. (0.0116 moles) of chlorine dissolved in 12 ml. of carbon tetrachloride are cooled to −30° C. and the solution of 1.44 g. (0.116 moles) of thioanisole in 10 ml. of dry dichloro methane is added dropwise at the same temperature. The obtained suspension is allowed to stir at −10° C. for 10 minutes, whereupon 1 g. (0.0058 moles) of 3,3aβ,4,5,6,6aβ-hexahydro-2-oxo-4β-hydroxymethyl-5α-hydroxy-2H-cyclopenta[a]furane in 15 ml. of acetonitrile is added at −30° C. The suspension slowly dissolves. The reaction mixture is stirred at −20° C. for 5 hours. The reaction is controlled by t.l.c. measurement after adding to an aliquot of the mixture triethyl amine, using the 2:1 mixture of ethyl acetate and methanol as eluent. Thereafter 2.3 g. (0.0232 moles) of triethyl amine in 10 ml. of dichloromethane are added to the reaction mixture dropwise, at −20° C. The suspension is stirred intensively for five minutes, whereupon the precipitated triethyl amine hydrochloride is filtered off. The filtrate is poured to the sodium salt of 1.3 g. of dimethoxy-2-oxo-hetpyl-phosphonate prepared in dry dimethoxy ethane (To the suspension of 0.7 g. (0.00585 moles) of sodium hydride (20% suspension in paraffin oil) in 15 ml. of dry dimethoxyethane there are added 1.3 g. (0.00585 moles) of dimethoxy-2-oxoheptyl-phosphonate dropwise, under vigorous stirring, then the mixture is stirred vigorously for 30 minutes). The reaction mixture is allowed to warm to room temperature then washed with brine, the organic phase is dried over sodium sulfate and is evaporated under reduced pressure. 4 g. of a dark-brown oily product are obtained which is passed through 50 g. of silica gel and eluated with a 2:1 mixture of ethyl acetate and petroleum ether. The fractions corresponding to $R_f=0.47$ are pooled and evaporated under reduced pressure. Yield: 1 g. (64.5%). The physical-chemical characteristics of the obtained product are identical with those of the named compound of Example 1.

EXAMPLE 4

3,3a$\beta$,4,5,6,6a$\beta$-hexahydro-2-oxo-4$\beta$-(3-oxo-trans-1-octene-1-yl)-5$\alpha$-hydroxy-2H-cyclopenta[b]furane (procedure of phosphonate type)

The procedure described in the Example 3 is applied but after filtering off the triethyl amine hydrochloride, the filtrate is evaporated at a temperature below 10° C., then the obtained residue is dissolved in 15 ml. of dimethoxy ethane or 10 ml. of aceto-nitrile and added to the dimethoxy-2-oxoheptyl-phosphonate sodium salt prepared as described in Example 3.

Yield: 0.84 g. (55%).

EXAMPLE 5

3,3a$\beta$,4,5,6,6a$\beta$-hexahydro-2-oxo-4$\beta$-(3-oxo-trans-1-octene-1-yl)-5$\alpha$-hydroxy-2H-cyclopenta[b]furane (oxidation with chromate)

935 mg. (0.0435 moles) of pyridine-chlorochromate complex are suspended in 15 ml. of dry dichloro methane at 0° C. 500 mg. (0.0029 moles) of 3,3a$\beta$,4,5,6,6a$\beta$-hexahydro-2-oxo-4$\beta$-hydroxymethyl-5$\alpha$-hydroxy-2H-cyclopenta[b]-furane are dissolved in 15 ml. of acetonitrile and the solution is added to the pyridine-chlorochromate suspension. Thereafter the mixture is vigorously stirred for 4 hours at 0° C. The dark precipitate is filtered off on a G-3 glass filter, and 1.62 g. (0.0043 moles) of triphenyl-n-hexanoylmethylene-phosphorane, dissolved in 5 ml. of methylene chloride, are added to the filtrate. The reaction mixture is allowed to stir for 3 hours at room temperature, then to stand overnight. The reaction mixture is washed subsequently with 2×30 ml. of hydrochloric acid, 30 ml. of 5% sodium bicarbonate solution and brine, the organic layer is dried over sodium sulfate and evaporated under reduced pressure. Yield: 1.8 g. The raw product is passed through 50 g. of silica gel and eluated with a 2:1 mixture of ethyl acetate and petroleum ether. The fractions corresponding to $R_f=0.47$ are pooled and evaporated under reduced pressure. The named compound is obtained as a yellow oil. Yield: 0.25 g. (33%).

The physical-chemical characteristics of the obtained product are identical with those of the named compound of the Example 1.

EXAMPLE 6

3,3a$\beta$,4,5,6,6a$\beta$-hexahydro-2-oxo-4$\beta$-(3-oxo-trans-1-octene-1-yl)-5$\alpha$-(4-phenyl-benzoyloxy)-2H-cyclopenta[b]furane 300 mg. (0.0013 moles) of 3,3a$\beta$,4,5,6,6a$\beta$-hexahydro-2-oxo-4$\beta$-(3-oxo-trans-1-octene-1-yl)-5$\alpha$-hydroxy-2H-cyclopenta[b]furane and 270 mg. (0.00124 moles) of 4-phenyl-benzoyl chloride are dissolved in 2.5 ml. of dry pyridine and the mixture is warmed to 60° C. and allowed to stir at this temperature for 30 minutes. By pouring an aliquot sample onto a small amount of n-hydrochloric acid and analyzing the obtained product by t.l.c. (ethyl acetate-petroleum ether 2:1), the reaction can be controlled. The pyridine is distilled off under reduced pressure, the residue is taken up in 30 ml. of methylene chloride, the methylene chloride solution is washed subsequently with 20 ml. of 1 N hydrochloric acid solution and 20 ml. of water, dried over sodium sulfate and evaporated under reduced pressure. The residue is recrystallized from 5 ml. of in isopropanol-petroleum ether mixture.

The named compound is a white crystalline compound.

Yield 450 mg. (89%).

Melting point: 81° to 82° C., $R_f=0.85$ (2:1 mixture of ethyl acetate and petroleum ether)

IR-spectrum (film): 1770 (=CO lactone), 1710 (—CO-ester), 1675 (=CO enon), 1630 (>C=C<enon), 975 (trans—CH=CH—), 730 and 700 (aromatic nucleus), cm$^{-1}$ NMR spectrum (CDCl$_3$) $\delta=7.2$—8.2 (compl. 9H, aromatic, 6.1–6.9 (d+dd, 2H, olefine), 5.38 (q, 1H, —$\overset{|}{C}$HOCO—ester), 5,1 (m, 1H, —$\overset{|}{C}$HOCO—lactone), 0.9 (t, 3H, —CH$_3$).

EXAMPLE 7

3,3a$\beta$,4,5,6,6a$\beta$-hexahydro-2-oxo-4$\beta$-(3-oxo-trans-1-octene-1-yl)-5$\alpha$-(4-phenyl-benzoyloxy)-2H-cyclopentane[b]furane (direct acylating)

The procedure described in Examples 1, 2, 3, 4 and 5 is followed but instead of using chromatography the following method is applied. 1 part by weight of the raw product is dissolved in 5 part by weight of pyridine and the solution is treated with an equivalent quantity of 4-phenyl-benzoyl chloride for 30 minutes at 60° C. The pyridine is distilled off under reduced pressure, the residue is taken up in 30 ml. of methylene chloride, the methylene chloride solution is washed subsequently with 20 ml. of 1 N hydrochloric acid solution and 20 ml. of water, then it is dried over sodium sulfate and the methylene chloride is distilled off. The residue is taken up in 15 ml. of ethyl acetate and the polar impurities are precipitated with 15 ml. of petroleum ether. The petroleum ether-ethyl acetate solution is evaporated, the residue is crystallized from 15 ml. of isopropanol-petroleum ether. The title compound is a white, crystalline compound. The physical-chemical characteristics of the obtained product are identical with those of the named compound of the Example 6.

What we claim is:

1. A process for the preparation of a racemic or optically active compound formula V,

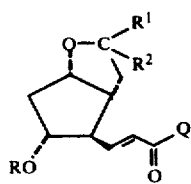
(V)

wherein
R is hydrogen, acyl, or silyl,
R¹ and R² together form an oxo group or
R¹ is lower alkoxy, which can be substituted with one, two or three halogen atom(s) and
R² is hydrogen,
Q is a straight or branched chained alkyl alkenyl or alkinyl having one to 10 carbon atoms, said alkenyl containing one double bond, said alkinyl containing one triple bond, which comprises reacting a racemic or optically active lactone diol derivative of formula III

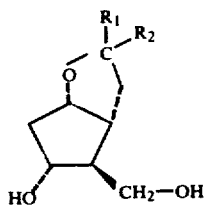
(III)

with an oxidant selected from the group which consists of thioanisole, effective sulfide complexes with chlorine, sulfoxides and effective chromium complex oxidants, then further reacting the thus obtained aldehyde of formula II

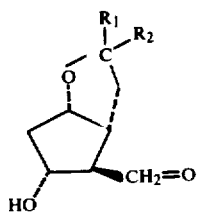
(II)

with a phosphorous compound of formula VI

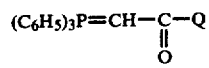
(VI)

or VII

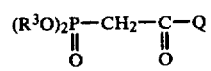
(VII)

wherein R³ is lower alkyl then acylating or silylating the hydroxyl of the obtained compounds of formula VIII

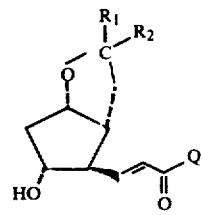
(VIII)

2. The process defined in claim 1 which comprises employing a thioanisole-chloro complex as the oxidant.

3. The process defined in claim 1 which comprises employing oxidants of sulfide or sulfoxide type.

4. The process defined in claim 1 which comprises employing chromium complexes as oxidants.

5. The process defined in claim 1 for the preparation of a compound of formula V, in which Q is n-pentyl which comprises employing triphenyl-n-hexanoyl-methylene-phosphorane as the phosphorous compound.

6. The process defined in claim 1 for the preparation of a compound of the formula V in which Q is n-pentyl, which comprises employing dimethyl-2-oxo-heptyl-phosphonate anion as the phosphorous compound.

7. The process defined in claim 1 for the preparation of racemic and optically active 3,3aβ,4,5,6,6aβ-hexahydro-2-oxo-4β-(3-oxo-trans-1-octene-1-yl)-5α-hydroxy-2H-cyclopenta[b]furane and 3,3aβ,4,5,6,6aβ-hexahydro-2-oxo-4β-(3-oxo-trans-1-octene-1-yl)-5α-(p-phenylbenzoyloxy)-2H-cyclopenta[b]furane, which comprises oxidizing racemic or optically active 3,3aβ,4,5,6,6aβ-hexahydro-2-oxo-4β-hydroxymethyl-5α-hydroxy-2H-cyclopenta[b]furane with a thioanisole-chloro-complex, reacting without isolation the obtained product with triphenyl-n-hexanoyl-methylene-phosporane, and isolating the obtained product.

8. The process defined in claim 1 wherein the isolated obtained product is acylated with p-phenyl-benzoyl chloride.

* * * * *